(12) United States Patent
Kang et al.

(10) Patent No.: US 8,367,355 B2
(45) Date of Patent: Feb. 5, 2013

(54) METHOD OF QUANTITATIVE ASSESSMENT ON REPRODUCTIVE EFFORT OF BLACK-LIP PEARL OYSTERS USING ANTIBODY SPECIFIC THERETO

(75) Inventors: Do Hyung Kang, Gyeonggi-Do (KR); Kwang Sik Choi, Jeju-Do (KR); Hee Do Jeoung, Jeju-Do (KR); Heung Sik Park, Seoul (KR)

(73) Assignee: Korea Ocean Research And Development Institute, Ansan, Gyeonggi-Do (KR)

( * ) Notice: Subject to any disclaimer, the term of this patent is extended or adjusted under 35 U.S.C. 154(b) by 116 days.

(21) Appl. No.: 12/759,589

(22) Filed: Apr. 13, 2010

(65) Prior Publication Data

US 2011/0097750 A1    Apr. 28, 2011

(30) Foreign Application Priority Data

Apr. 14, 2009  (KR) .................. 10-2009-0032425
Dec. 3, 2009   (KR) .................. 10-2009-0119138

(51) Int. Cl.
| | |
|---|---|
| C07K 7/06 | (2006.01) |
| C07K 16/02 | (2006.01) |
| C07K 16/18 | (2006.01) |
| G01N 33/53 | (2006.01) |
| G01N 33/543 | (2006.01) |
| G01N 33/567 | (2006.01) |

(52) U.S. Cl. ...... 435/7.92; 435/7.1; 435/7.21; 435/7.95; 436/503; 436/518; 436/65; 530/328; 530/350; 530/387.9; 530/389.1; 530/857

(58) Field of Classification Search .................. 435/7.1, 435/7.21, 7.92, 7.95; 436/503, 518, 65; 530/328, 530/350, 387.9, 389.1, 857
See application file for complete search history.

(56) References Cited

U.S. PATENT DOCUMENTS 7,163,795 B2    1/2007 Chang et al.

2003/0027258 A1   2/2003 Chang et al.
2005/0282183 A1   12/2005 Change et al.

FOREIGN PATENT DOCUMENTS

JP    2009-219487 A    10/2009
WO    96-15662 A1    5/1996

OTHER PUBLICATIONS

Jung, Hui Do et al., "Polyclonal antibody development of egg protein of *Pinctada margaritifera* inhabit the South Pacific Micronesua Chuuk" Fishery Sciences Association of Korea Joint Conference Abstract in 2008, p. 434, poster No. 16 (Nov. 13, 2008).
Park, K. et al., "Quantification of reproductive output of the butter clam, *Saxidomus purouratus* (Sowerby, 1852) using enzyme-linked immunosorbent assay (ELISA)" Ocean and polar research, vol. 25, No. 3, pp. 249-456 (Sep. 2003).
Duplat et al., "Identification of calconectin, a calcium-binding protein specifically expressed by the mantle of *Pinctada margaritifera*," FEBS Letters, 580, pp. 2435-2441 (2006).
Kang et al., "Enzyme-linked immunosorbent assay (ELISA) used in quantification of reproductive output in the pacific oyster, *Crassostrea gigas*, in Korea," Jrl. of Experimental Marine Biology and Ecology, 282(2003) 1-21.
Park et al., "Application of enzyme-linked immunosorbent assay for studying of reproduction in the Manila clam *Ruditapes philippinarum* (Mollusca: Bivalvia) I. Quantifying eggs," Aquaculture, 241, pp. 667-687 (2004).
Office Action for Japanese Patent Application No. 2010-9212, dated May 25, 2010.

*Primary Examiner* — Gail R Gabel
*Assistant Examiner* — James L Grun
(74) *Attorney, Agent, or Firm* — Edwards Wildman Palmer LLP

(57) ABSTRACT

Disclosed are an antigen protein of black-lip pearl oyster egg extract, an antibody specific thereto, and a method of quantitative assessment of the reproductive effort of black-lip pearl oyster using the antibody. The method accomplishes quantitative assessment of reproductive effort of black-lip pearl oysters easily and accurately. In addition, the method provides important information for the study of life cycles of black-lip pearl oysters, and allows efficient management of black-lip pearl oysters.

11 Claims, 6 Drawing Sheets

SEQUENCE LISTING

<160> NUMBER OF SEQ ID NOS: 8

<210> SEQ ID NO 1
<211> LENGTH: 10
<212> TYPE: PRT
<213> ORGANISM: Pinctada margaritifera

<400> SEQUENCE: 1

Phe Lys Pro Phe Arg Glu Glu Lys Asp Arg
 1               5                   10

<210> SEQ ID NO 2
<211> LENGTH: 10
<212> TYPE: PRT
<213> ORGANISM: Pinctada margaritifera

<400> SEQUENCE: 2

Asp Lys Pro Phe Arg Glu Glu Lys Asp Arg
 1               5                   10

<210> SEQ ID NO 3
<211> LENGTH: 10
<212> TYPE: PRT
<213> ORGANISM: Pinctada margaritifera

<400> SEQUENCE: 3

Phe Ile Pro Phe Arg Glu Glu Lys Asp Arg
 1               5                   10

<210> SEQ ID NO 4
<211> LENGTH: 10
<212> TYPE: PRT
<213> ORGANISM: Pinctada margaritifera

```
<400> SEQUENCE: 4

Asp Ile Pro Phe Arg Glu Glu Lys Asp Arg
 1               5                   10

<210> SEQ ID NO 5
<211> LENGTH: 10
<212> TYPE: PRT
<213> ORGANISM: Pinctada margaritifera

<400> SEQUENCE: 5

Phe Lys Pro Phe Arg Glu Ser Lys Asp Arg
 1               5                   10

<210> SEQ ID NO 6
<211> LENGTH: 10
<212> TYPE: PRT
<213> ORGANISM: Pinctada margaritifera

<400> SEQUENCE: 6

Asp Lys Pro Phe Arg Glu Ser Lys Asp Arg
 1               5                   10

<210> SEQ ID NO 7
<211> LENGTH: 10
<212> TYPE: PRT
<213> ORGANISM: Pinctada margaritifera

<400> SEQUENCE: 7

Phe Ile Pro Phe Arg Glu Ser Lys Asp Arg
 1               5                   10

<210> SEQ ID NO 8
<211> LENGTH: 10
<212> TYPE: PRT
<213> ORGANISM: Pinctada margaritifera

<400> SEQUENCE: 8

Asp Ile Pro Phe Arg Glu Ser Lys Asp Arg
 1               5                   10
```

METHOD OF QUANTITATIVE ASSESSMENT ON REPRODUCTIVE EFFORT OF BLACK-LIP PEARL OYSTERS USING ANTIBODY SPECIFIC THERETO

CROSS-REFERENCE TO RELATED APPLICATION

This application claims under 35 U.S.C. §119(a) the benefit of Korean Application Nos. 10-2009-0032425 filed Apr. 14, 2009 and 10-2009-0119138 filed Dec. 3, 2009, the entire contents of which are incorporated herein by reference.

BACKGROUND OF THE INVENTION

1. Field of the Invention

The present invention relates to an antigen protein of black-lip pearl oyster egg extract, and a method of quantitative assessment on the reproductive effort of black-lip pearl oyster using an antibody specific thereto.

2. Description of the Prior Art

Black-lip pearl oysters (*Pinctada margaritifera*) inhabiting over the coral area of the Indo-Pacific are very large in size as compared to other species, and thus can produce significantly larger pearls. Accordingly, production of black pearls through the culture of black-lip pearl oysters becomes one of the most important industries in the South Pacific island states. The annual average production of black-lip pearl oysters reaches 6 M/T (metric ton, US $175,000,000). Such an increase in the production of black pearls causes a rapid increase in the demand of mother of pearl and a decrease in the amount of black-lip pearl oyster resources.

Thus, in the field of the industry of pearl culture in the South Pacific Chuuk Lagoon, it is one of the imminent things to supply mother of pearl stably for the production of black pearls. Recently, in the South Pacific Chuuk Lagoon, a natural seed collection method, in which floating spats discharged from naturally occurred black-lip pearl oysters are collected, has been frequently used as a method for the culture of black-lip pearl oysters. However, it is difficult to obtain spats in an amount sufficient for the culture industry. Under these circumstances, there has been a great need for the production of spats through the introduction of artificial seed production and stable supply of the spats of black-lip pearl oysters. However, the artificial seed production of black-lip pearl oysters has not been accomplished successfully to date because of the lack of the fundamental study of life cycles and reproduction physiology of black-lip pearl oysters. In addition, since the study of the reproduction of Bivalvia distributed over the tropical zone is significantly poor, as compared to the Bivalvia of the temperate zone, information about the strategy of reproduction of tropical Bivalvia or the physiological characteristics thereof is absolutely insufficient.

Therefore, physiological studies of reproduction of mother of pearl for the production of high-quality seeds should be performed in order to control the black-lip pearl oyster resources successfully. Such studies include a qualitative study, such as understanding the annual reproduction cycle of mother of pearl and predicting the breeding season, as well as quantitative determination of eggs and sperms produced from mother of pearl, i.e., determination of reproductive effort or fecundity. Particularly, the study of determination of reproductive effort is poorer than qualitative studies due to the difficulty unique to such determination. This is because most Bivalvia has an ovary containing eggs, which is not separated physically from other organs but is included in the pallial membrane or digestive diverticulum, and the fecundity of Bivalvia reaches several millions or several tens of millions.

SUMMARY OF THE INVENTION

Accordingly, the present invention has been made to solve the above-mentioned problems occurring in the prior art, and the present invention provides an antibody specifically responsive to an egg protein of black-lip pearl oysters (*Pinctada margaritifera*), a kind of Bivalvia, and a method of quantitative determination of reproductive effort of black-lip pearl oysters.

In other words, an object of the present invention is to provide an antigen protein of black-lip pearl oyster egg extract.

Another object of the present invention is to provide an antibody specific to the antigen protein of black-lip pearl oyster egg extract.

Still another object of the present invention is to provide a method of quantitative assessment of reproductive effort of black-lip pearl oysters by using the antibody.

To achieve the objects of the present invention, one aspect of the present invention provides an antigen protein of black-lip pearl oyster egg extract represented by the amino acid sequence of:

[X-Y-Pro-Phe-Arg-Glu-Z-Lys-Asp-Arg], wherein X is Phe or Asp;
Y is Lys or Ile;
Z is Glu or Ser;
Pro is the abbreviation of proline;
Phe is the abbreviation of phenylalanine;
Arg is the abbreviation of arginine;
Glu is the abbreviation of glutamic acid;
Lys is the abbreviation of lysine;
Asp is the abbreviation of aspartic acid;
Ile is the abbreviation of isoleucine; and
Ser is the abbreviation of serine.

Particularly, according to the amino acid sequence, an antigen protein of black-lip pearl oyster egg extract represented by Seq. Nos. 1-8 is provided.

In another aspect, the present invention provides an antibody specific to the antigen protein.

In still another aspect, the present invention provides a method of quantitative assessment of reproductive effort of black-lip pearl oysters, including the steps of:
(i) determining an amount of an egg protein of black-lip pearl oysters via an antigen-antibody reaction using the antibody; and
(ii) estimating an actual amount of the egg protein of black-lip pearl oysters through a standard curve plotted between the amount of the egg protein of black-lip pearl oysters determined in step (i) and an actual amount thereof.

The antibody-antigen reaction that may be used herein includes enzyme-linked immunosorbent assay (ELISA) but is not limited thereto. More particularly, the method of quantitative assessment of reproductive effort of black-lip pearl oysters according to one embodiment of the present invention includes carrying out quantitative analysis of a specific egg protein participating in the maturation of eggs of black-lip pearl oysters by ELISA using the antibody according to the present invention, so that the total amount of the specific egg protein can be obtained in an indirect manner. Such a total amount of the specific egg protein obtained indirectly is used to estimate an actual amount of the egg protein via a standard curve plotted between actual amounts and indirect amounts. Then, the fecundity (reproductive effort) can be estimated from the amount of the egg protein contained in an individual.

The method of quantitative assessment of reproductive effort of black-lip pearl oysters according to the present invention uses a specific antigen-antibody reaction to accomplish quantitative assessment of reproductive effort of black-lip pearl oysters easily and accurately. In addition, the method according to the present invention provides important information for the efficient management of black-lip pearl oysters producing black pearls and for the study of their life cycles.

BRIEF DESCRIPTION OF THE DRAWINGS

The above and other objects, features and advantages of the present invention will be more apparent from the following detailed description taken in conjunction with the accompanying drawings, in which:

FIGS. 3A and 3B are photographs showing the results of western blotting according to an embodiment of the present invention (FIG. 3A: before the removal of cross-reactivity, FIG. 3B: after the removal of cross-reactivity, 1: egg protein, 2: molecular weight marker, 3: somatic tissue extract, 4: digestive gland extract, 5: male gonad extract);

DETAILED DESCRIPTION OF THE EXEMPLARY EMBODIMENTS

Figure 1:
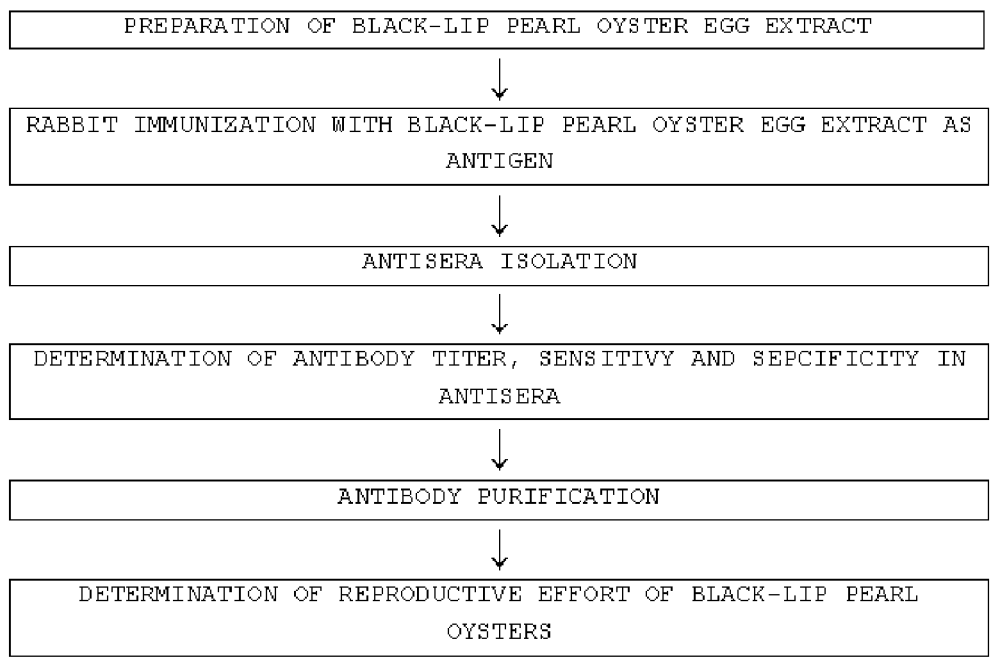
FIG. 1 is the overall flow chart of an embodiment of the present invention.

Although an exemplary embodiment of the present invention has been described for illustrative purposes, those skilled in the art will appreciate that various modifications, additions and substitutions are possible, without departing from the scope and spirit of the invention as disclosed in the accompanying claims.

EXAMPLES

Example 1

Preparation of Black-Lip Pearl Oyster Egg Extract 1-1: Separation of Eggs

Around an April day, which is the age of maturity of black-lip pearl oysters, 30 individuals of black-lip pearl oysters are collected from a long-line hanging type farm in the Chuuk state, Federated States of Micronesia. Twelve individuals of female mother of pearl are used in the present invention, and each has a size of 105.3-155.7 mm.

First, the shells of black-lip pearl oysters are removed, and a portion of sexual gland tissues is taken to separate male one and female one from each other. The portion of matured female ovary is cut out and is placed on a Petri dish. The surface of the ovary sample is cut into a fine check pattern by using a razor blade, and is pressurized with a soft bar to extract the eggs. The eggs separated in the above manner are mixed with 0.02 mM aqueous ammonium hydroxide and a predetermined amount of sea water (filtered through a 0.45 µm sieve and then sterilized), and the resultant mixture is filtered through a sieve having an eye size of 100 µm to remove crude impurities. Then, the mixture of eggs and sea water is further filtered through a sieve having an eye size of 40 µm to remove fine impurities other than the eggs, and then is subjected to centrifugal separation at a low speed (100 rpm, 10 minutes), thereby removing the remaining impurities in the supernatant. After that, the purified black-lip pearl oyster eggs are frozen at $-75°$ C., and are lyophilized by using a freeze-drier.

1-2: Biochemical Compositional Analysis of Black-Lip Pearl Oyster Eggs (1) Analysis for Total Carbohydrate Content The total carbohydrate content is analyzed by the Phenol-Sulfuric acid method (Taylor (1955)). To the lyophilized powder of black-lip pearl oyster eggs, PBS (phosphate buffered saline) is added. Next, the resultant mixture is homogenized by an ultrasonic homogenizer and is subjected to centrifugal separation, and then the supernatant is collected. Then, phenol and sulfuric acid solution are added to the supernatant to perform color development, and the absorbance is measured by a spectrophotometer at a wavelength of 490 nm. Anhydrous dextrose is diluted to a concentration of 50-1000 µg/ml the diluted solutions are used as standards. The total carbohydrate content (mg/g tissue dry weight, TDW) of a sample is calculated according to the interrelation between the carbohydrate concentrations of dextrose standards and the absorbances.

(2) Analysis for Total Protein Content

The total protein content is analyzed in the following manner. First, 0.1M sodium hydroxide (NaOH) solution is added to the lyophilized powder of black-lip pearl oyster eggs, the resultant mixture is incubated at $37°$ C. for 2 hours and is subjected to centrifugal separation, and then the supernatant is collected. The absorbance of the supernatant is measured by using a BCA protein assay kit (Pierce, 23227) and a spectrophotometer at a wavelength of 562 nm. Then, the total protein content (mg/g TDW) of a sample is calculated according to the interrelation between the protein concentrations (50-1000 µg/ml) of BSA (bovine serum albumin) standards and the absorbances.

(3) Analysis for Total Fat Content

The total fat content is analyzed in the following manner. A mixture of chloroform and methanol is added to the lyophilized powder of black-lip pearl oyster eggs to extract the whole fat of the sample. Next, 0.9% sodium chloride (NaCl) solution is added thereto to separate the mixture into two phases, i.e., a chloroform phase and a methanol-water phase. The upper methanol-water phase is discarded and the chloroform phase containing fat dissolved therein is collected. The fat-containing chloroform phase is poured into an aluminum dish and dried in a drier for one day to remove chloroform. Then, the amount of fat (mg/g TDW) is determined by subtracting the weight of the dish.

As shown in the following Table 1, the biochemical compositional analysis of black-lip pearl oyster eggs reveals that the total protein content is 40-51%, the total carbohydrate content is 4-10%, and the total fat content is 20-22%.

TABLE 1

|  | Protein | Carbohydrate | Fat |
|---|---|---|---|
| Amount (%) | 45.5 | 7 | 21.5 |

Example 2

Analysis for Amino Acid Sequences of Antigen Protein of Black-Lip Pearl Oyster Egg Extract The black-lip pearl oyster egg extract separated from Example 1-1 is analyzed and the antigen proteins of the egg extract are shown in FIGS. 3A and 3B and FIGS. 4A and 4B. Then, amino acid sequences of the protein specific to the black-lip pearl oyster eggs are analyzed. After the analysis, the amino acid sequences of 23 kD protein are determined and the results are shown in the following Table 2. Herein, the amino acid sequences are analyzed in a manner known to those skilled in the art.

TABLE 2

```
Seq. No.   Amino Acid Sequence

Seq. No. 1   Phe Lys Pro Phe Arg Glu Glu Lys Asp Arg

Seq. No. 2   Asp Lys Pro Phe Arg Glu Glu Lys Asp Arg

Seq. No. 3   Phe Ile Pro Phe Arg Glu Glu Lys Asp Arg

Seq. No. 4   Asp Ile Pro Phe Arg Glu Glu Lys Asp Arg

Seq. No. 5   Phe Lys Pro Phe Arg Glu Ser Lys Asp Arg

Seq. No. 6   Asp Lys Pro Phe Arg Glu Ser Lys Asp Arg

Seq. No. 7   Phe Ile Pro Phe Arg Glu Ser Lys Asp Arg

Seq. No. 8   Asp Ile Pro Phe Arg Glu Ser Lys Asp Arg
```

It is thought that the proteins having a different size are not analyzed because of the presence of modification, such as methylation, glycosylation, alkylation or acetylation, at the side of N-terminal.

Example 3

Preparation of Antibody

First, PBS is added to the lyophilized powder of black-lip pearl oyster eggs obtained from Example 1-1. Next, the mixture is homogenized by an ultrasonic homogenizer and is subjected to centrifugal separation, and then the supernatant is collected. Then, the supernatant is diluted to a concentration of 0.5 mg/ml of the black-lip pearl oyster egg protein extract. Then, 0.5 ml of the black-lip pearl oyster egg protein extract is mixed with the same amount of Freund's complete adjuvant (FCA), and the resultant mixture is injected to 4-5 sites of the back of a rabbit via a subcutaneous route. Herein, the blood taken from the artery of the rabbit's ear before the initial injection is used as a control. Two weeks after the initial injection, the same mixture of the antigen protein with Freund's complete adjuvant is further injected four times as a whole.

Meanwhile, the antibody is constructed in the manner as shown in Table 3. During the construction of the antibody, blood samples are taken from the artery of the rabbit's ear and the sera are separated.

TABLE 3

| Time | Treatment | Serum Collection |
|---|---|---|
| 0 week | Initial inoculation | |
| 2 weeks after | First additional immunization | ○ |
| 4 weeks after | Second additional immunization | ○ |
| 5 weeks after | Third additional immunization | |
| 7 weeks after | Fourth additional immunization | |
| 8 weeks after | | ○ |
| 9 weeks after | | ○ |
| 13 weeks after | | ○ |

Example 4

Determination of Effect of Antibody and Purification of Antibody 4-1: Hemagglutination Test To determine the presence of an antibody in sera and the titer of the antibody, a hemagglutination test is carried out. The blood used in this test is red blood cells isolated from human blood. Approximately 3 ml of human blood is taken in a tube treated with EDTA or heparin, washed with PBS three times, and is subjected to centrifugal separation, thereby isolating red blood cells (RBC). The red blood cells isolated in this manner is allowed to float on PBS to a concentration of 1%, and is stabilized by adding formalin to 1% RBC. Then, the formalin-treated 1% RBC is mixed with 0.05 mg/ml of tannic acid at a ratio of 1:1 so that the red blood cells are coated. After that, the same amount of black-lip pearl oyster egg protein extract as an antigen is added to the coated red blood cells, followed by incubation at room temperature for 10 minutes. The sera taken at the serum collection times as shown in Table 3 are diluted at 100×, and heat treated at 56° C. for 30 minutes so that the complement is deactivated. The sera are diluted twice on a 96-well plate, and the pre-coated red blood cells are pipetted to the 2× diluted 96-well plate, each in an amount of 10 μl. Then, the hemagglutination is observed after 3 hours. The results are shown in FIG. 2.

Figure 2:
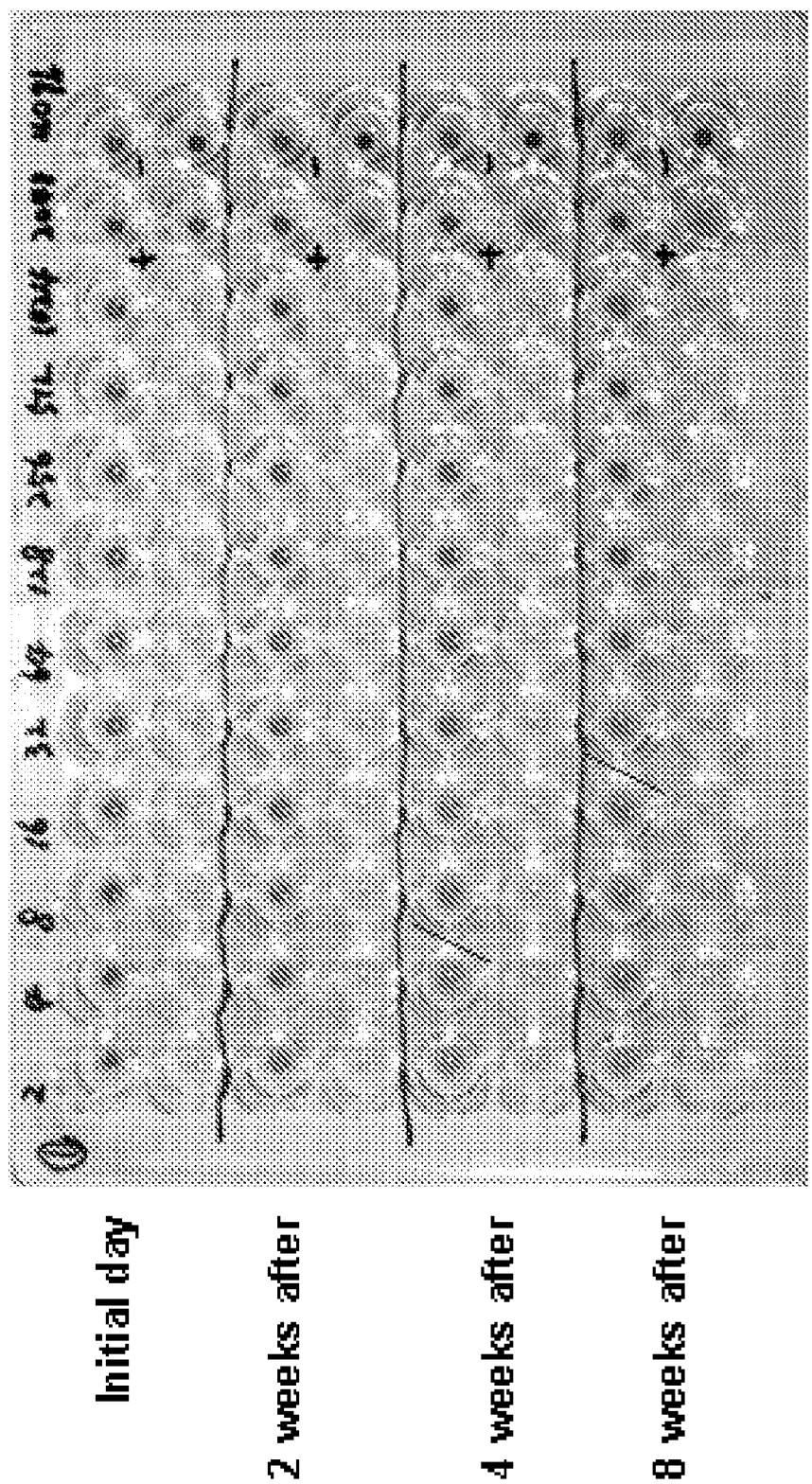
FIG. 2 is a photographic view showing the results of the hemagglutination test according to an embodiment of the present invention.

In FIG. 2, the sera taken before the injection of the antigen protein used as the control and those taken from 2 weeks after the injection show that no antibody-antigen agglutination occurs, and thus the results are shown in the form of dots of red blood cells collected on the bottom. The antibody-antigen agglutination occurs from the time of 4 weeks after the injection, and the antibody titer increases in the form of spread over the bottom of the 96-well plate. Herein, only the form of complete spread is regarded as the occurrence of antibody-antigen agglutination. Meanwhile, 8 weeks after the injection, the test sensitivity is such a degree that the antibody titer is observed until the dilution is 1:6000.

4-2: Removal of Immunosorbent Cross-reactivity and Isolation of IgG

Cross-reactions with tissue cells other than eggs function as a factor of overvalue in measuring the reproductive effort. In the case of black-lip pearl oysters, they have an annual spawn tendency, and thus any individuals in a non-differentiated phase containing no eggs cannot be used. Thus, such cross-reactions are removed with a glutaraldehyde immunosorbent using male individuals and having male individual extract attached thereto.

First, 5 g of lyophilized male individuals is dissolved in ml of PBS and is homogenized by using an ultrasonic homogenizer. The homogenized mixture is subjected to centrifugal separation under 4500 rpm for 10 minutes. To the male individual extract obtained as described above, 10 ml of 2M sodium acetate buffer (pH 5.0) is added and 4 ml of 25% glutaraldehyde is further added thereto gradually to perform a reaction for 3 hours. Next, the reaction mixture is washed with PBS to remove the remaining protein non-bound with glutaraldehyde. Then, 200 ml of 0.2M glycine buffer (pH 2.8) is added thereto as an eluting agent, 100 ml of 1M $K_2HPO_4$ is added thereto for the purpose of pH adjustment, and 100 ml of 1M ethanolamine is further added thereto. The reaction mixture is allowed to react overnight to prepare an immunosorbent. The immunosorbent prepared in the above manner is allowed to react with the same amount of sera diluted twice at room temperature for 3 hours. The reaction mixture is subjected to centrifugal separation under 3000 rpm for 5 minutes, the supernatant is collected, and NaOH is added thereto to adjust the pH to about 6.

Subsequently, to isolate immunoglobulin G (referred to also as IgG) from the sera free from cross-reactivity, 100% saturated ammonium sulfate (($NH_4)_2SO_4$) solution is diluted to a concentration of 40% and the sera is allowed to react with 40% ammonium sulfate solution at 4° C. for 6 hours to precipitate IgG. Then, centrifugal separation (4000 rpm, 30 minutes) is carried out to obtain IgG. After that, PBS is added thereto in an amount corresponding to about 50% of the amount of sera taken initially before the removal of the cross-reactivity, so that IgG floats again thereon, and then dialysis is performed for one day by using a dialysis tubing to complete the isolation of IgG. The isolated IgG is frozen and stored before the analysis.

4-3: Western Blot 4-3-1. Determination of Cross-Reactivity with Other Tissues

To investigate the molecular characteristics of the black-lip pearl oyster egg protein, incontinuous SDS-PAGE is carried out. In addition, western blotting is carried out to determine which portion is specific to the antibody according to the present invention, and whether any cross-reactivity with other tissues is present or not. The sample before the removal of cross-reactivity is compared with the sample after the removal of cross-reactivity on the basis of western blotting to determine whether the cross-reactivity is removed successfully or not.

PBS is introduced into each lyophilized powder of black-lip pearl oyster eggs, other tissues (foot, gill, mantle and muscle), digestive diverticulum, and male testis. Next, the resultant mixture is homogenized with an ultrasonic homogenizer and is subjected to centrifugal separation. Then, each supernatant is collected and diluted to a protein concentration of 2 µg/ml. Each extract prepared as described above is pipetted in an amount of 10 µl, is subjected to SDS-PAGE, and then is transferred to a PVDF membrane (PIERCE, 88114).

Next, the membrane is blocked with 5% skim milk for 1 hour. Then, the antibody developed as a primary antibody after the removal of cross-reactivity in Example 4-2, i.e., the antibody specific to the black-lip pearl oyster egg protein according to the present invention (rabbit sera in development is used before the removal of cross-reactivity), is diluted with 5% skim milk to a ratio of 1:1000 (1:5000 before the removal of cross-reactivity). The blocked membrane is allowed to react with the antibody for 2 hours, followed by washing.

Then, a secondary antibody (goat anti-rabbit IgG HRP, KOMA) is diluted with a washing buffer to a ratio of 1:3000 and a reaction is carried out for 1 hour. After the washing, a mixture containing peroxidase and luminal at a ratio of 1:1 is sprayed to the membrane to perform a reaction for about 1-2 minutes, and then the ECL (electrogenerated chemiluminescence) reaction is filmed in a dark room for 3 minutes at an interval of 30 seconds.

Figure 3:
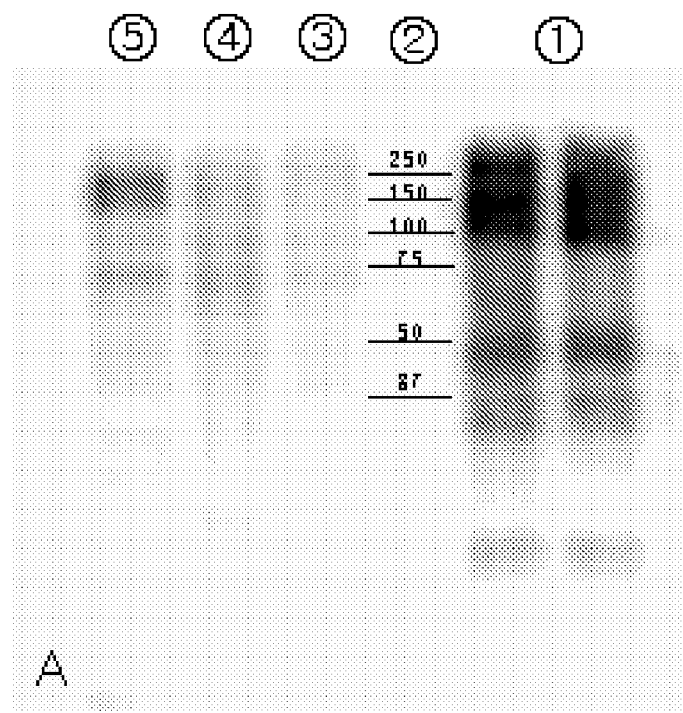
FIG. 3 is a photographic view showing the results of western blotting according to an embodiment of the present invention (A: before the removal of cross-reactivity, B: after the removal of cross-reactivity, 1: egg protein, 2: molecular weight marker, 3: somatic tissue extract, 4: digestive gland extract, 5: male gonad extract)
Figure 3:
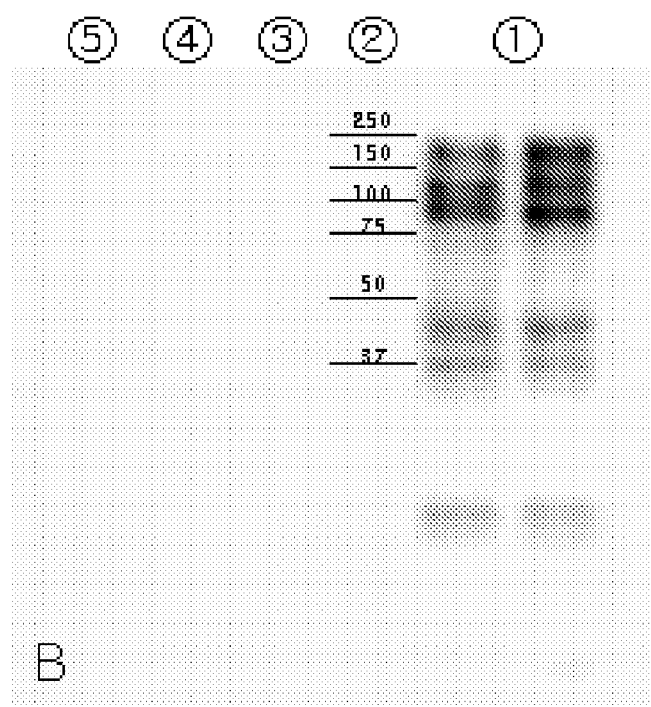
Figure 4:
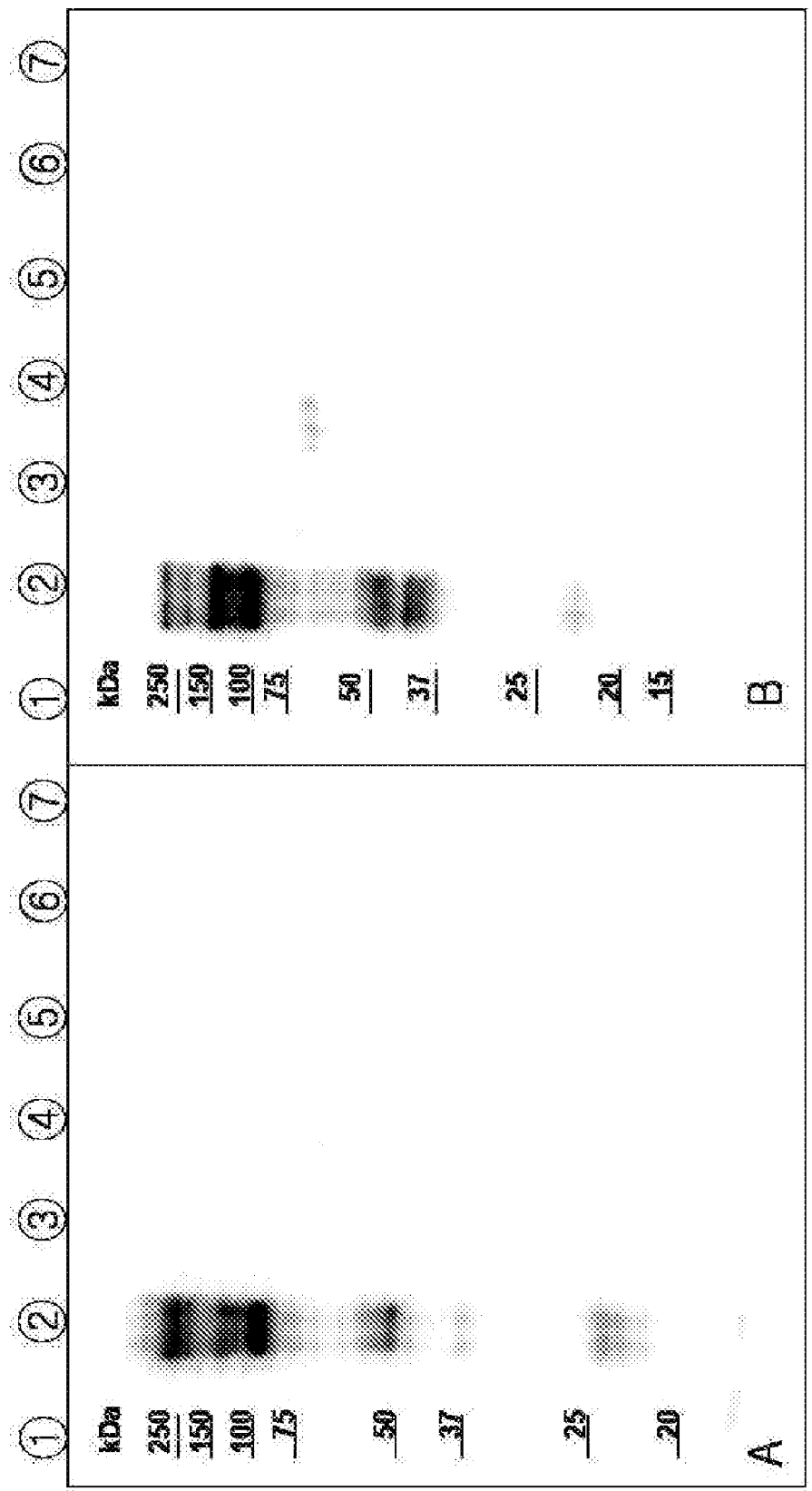
FIGS. 4A and 4B are photographs showing the results of western blotting according to an embodiment of the present invention (FIG. 4A: non-reducing condition, FIG. 4B: reducing condition, 1: molecular weight marker, 2: egg extract of *P. margaritifera*, 3: egg extract of *C. gigas*, 4: egg extract of *C. ariakensis*, 5: egg extract of *S. kegaki*, 6: egg extract of *M. edulis*, 7: egg extract of *R. pilippinarum*)

Meanwhile, FIGS. 3A and 3B are the photographs taken before and after the removal of cross-reactivity, respectively. FIG. 3A shows that cross-reactions with tissues other than the egg protein occur. On the contrary, FIG. 3B demonstrates that cross-reactions with tissues other than the egg protein disappear.

4-3-2. Determination of Cross-Reactivity with Other Species

To determine whether the antibody according to the present invention has cross-reactivity with egg proteins of other bivalve species, western blotting is carried out.

Each egg extract of *Pinctada margaritifera* and other species (*C. gigas; C. ariakensis; S. kegaki; M. edulis; R. philippinarum*) is taken in an amount of 10 µl and is subjected to SDS-PAGE. Then, western blotting is carried out in the same manner as described in Example 4-3-1. Finally, it can be seen from FIGS. 4A and B that the antibody according to the present invention has no cross-reactivity with egg proteins of bivalve species other than the egg protein of *Pinctada margaritifera*.

Particularly, it can be seen from the study of comparison with the egg proteins of other bivalve species that the black-lip pearl oyster egg protein of 23 kD, whose amino acid sequence is analyzed in Example 2, exists specifically in black-lip pearl oyster eggs (see Table 4).

TABLE 4

| Species | Molecular Weight (kDa) | Reference |
|---|---|---|
| *P. margaritifera* | Native PAGE: 420<br>Non-reducing condition:<br>270, 140, 95, 50, 37, 24<br>Reducing condition: 270,<br>150, 100, 47, 44, 23* | The present invention |
| *C. gigas* | 105, 85, 66, 64, 60, 45, 41 | Suzuki et al. 1992 |
| *C. ariakensis* | 150, 120, 95, 90, 82, 55 | Kim et al.<br>In preparation |
| *C. ariakensis* | Non-reducing condition:<br>260, 240, 90, 85, 53, 48,<br>42, 32<br>Reducing condition: 70, 73,<br>48, 45, 35, 30 | Mausumi and Choi.<br>In preparation |
| *C. virginica* | 76, 56, 50, 48, 18, 17 | Lee and Heffernan 1991 |
| *P. yessoensis* | 270, 60, 30 | Osada et al. 1992 |
| *S. purpuratus* | Non-reducing condition:<br>163, 95<br>Reducing condition: 247,<br>200, 99, 91, 54, 47 | Park et al. 2003 |
| *M. mercenaria* | 98, 87, 68, 60, 56, 36, 19 | Lee and Heffernan 1991 |
| *R. pilippinarum* | Non-reducing condition:<br>475, 84, 40<br>Reducing condition: 330,<br>96, 64, 50, 31 | Park and Choi 2004 |

*Black-lip pearl oyster egg protein of 23 kD, whose amino acid sequence is analyzed in Example 2.

4-4. ELISA (Enzyme Linked Immunosorbent Assay)

Figure 5A:
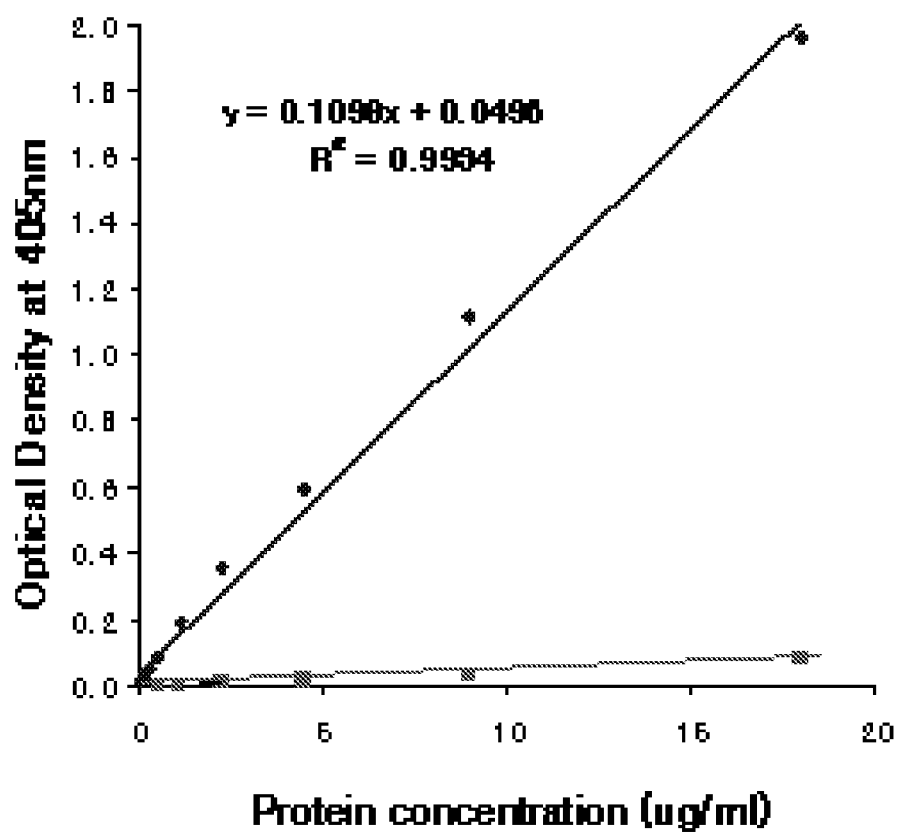
FIGS. 5A and 5B are graphs showing the results of ELISA according to an embodiment of the present invention (FIG. 5A: before the removal of cross-reactivity, FIG. 5B: after the removal of cross-reactivity, blue line: reaction with egg extract, pink line: reaction with somatic tissue extract).
Figure 5B:
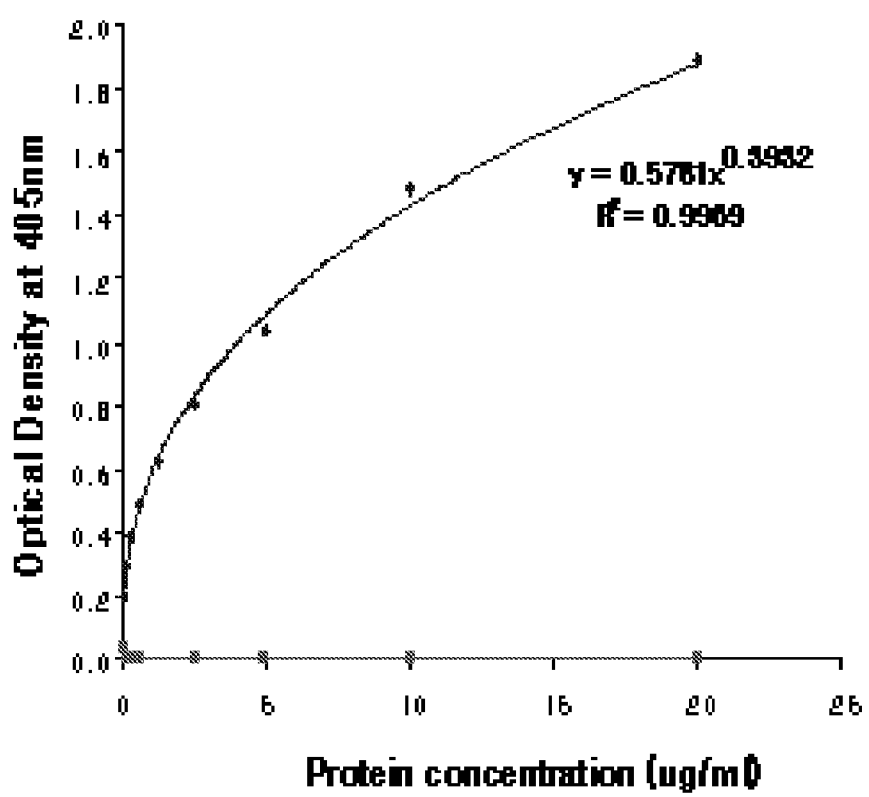

To determine the sensitivity of the antibody specific to black-lip pearl oyster egg protein, cross-reactivity with non-specific cells other than eggs is investigated by ELISA. As an antigen protein, black-lip pearl oyster egg protein is used after diluting it with PBS-T (PBS containing 0.05% Triton X-100). Male individual tissue extract is used as a control. Before the removal of cross-reactivity, 18 µg/ml of the egg protein and 22.5 µg/ml of the male individual tissue extract are diluted twice. After the removal of cross-reactivity, 20 µg/ml of the egg protein and 20 µg/ml of the male individual tissue extract are diluted twice. Then, they are used as antigen proteins. Such diluted antigen proteins are introduced to a 96-well ELISA microplate (polystyrene), each in an amount of 100 µl/ml, and are allowed to react overnight at 4° C. The microplate is washed with PBS-T by using a microplate autowasher. Then, 150 µl of 0.1% BSA (in PBS-T) is added thereto to perform blocking for 1 hour, and washing is carried out in the same manner as described above. After that, 100 µl of the antibody (concentration: 6.3 µg/ml) developed as a primary antibody after the removal of cross-reactivity in Example 4-2, i.e., the antibody specific to the black-lip pearl oyster egg protein according to the present invention is added thereto (12.8 µg/ml of sera is used before the removal of cross-reactivity). After carrying out a reaction for 1 hour, the microplate is washed. Then, 100 µl of a secondary antibody (concentration 1 µg/ml) (goat anti-rabbit IgG alkaline phosphate-conjugated) is further introduced thereto and a reaction is carried out for 1 hour. The absorbance is measured at 405 nm by using p-nitrophenyl phosphate (pNPP) as a color developing agent. It can be seen from the ELISA analysis that 0.14-18 µg/ml of egg protein is measured before the removal of cross-reactivity, while 2.8-22.5 µg/ml of egg protein is measured in the negative control. This suggests that a week cross-reaction occurs. However, it can be seen that 0.07-20 µg/ml of black-lip pearl oyster egg protein is measured after the removal of cross-reactivity, while no egg protein is measured in the negative control (FIGS. 5A and 5B).

4-5: Immunofluorescence Staining

Immunofluorescence staining is carried out on tissue slides before and after the removal of cross-reactivity to determine whether the antibody according to the present invention is specific to eggs or not. The tissue slide is freed from paraffin with xylene and is substituted with PBS-T through alcohol dehydration. The tissue slide is blocked with 5% BSA for 1 hour and washed three times with PBS-T. As a primary antibody, the antibody (concentration: 1 mg/ml) obtained after the removal of cross-reactivity in Example 4-2 (1.2 mg/ml of sera is used before the removal of cross-reactivity) is sprayed to the tissue slide in such a manner that the tissue is covered with the antibody, and is allowed to react with the tissue slide for 1 hour. After the tissue slide is washed with PBS-T, a secondary antibody (fluorescein isothiocyanate-conjugated goat antibody to rabbit IgG) is diluted with the blocking buffer to a ratio of 1:4000, the dilution is sprayed to the tissue slide in such a manner that the tissue is covered with the antibody, and then the secondary antibody is allowed to react with the tissue slide for 1 hour. Then, the tissue slide is washed with PBS-T, and is mounted in 50% glycerol. After that, the tissue slide is filmed by an optical microscope and the resultant photograph is observed under a fluorescence microscope.

While the present invention has been described with respect to the specific embodiments, it will be apparent to those skilled in the art that various changes and modifications may be made without departing from the spirit and scope of the invention as defined in the following claims.

What is claimed is:

1. An isolated antigen protein of black-lip pearl oyster egg extract, consisting of the amino acid sequence of Seq. Id. No.1.

2. An isolated antigen protein of black-lip pearl oyster egg extract, consisting of the amino acid sequence of Seq. Id. No.2.

3. An isolated antigen protein of black-lip pearl oyster egg extract, consisting of the amino acid sequence of Seq. Id. No.3.

4. An isolated antigen protein of black-lip pearl oyster egg extract, consisting of the amino acid sequence of Seq. Id. No.4.

5. An isolated antigen protein of black-lip pearl oyster egg extract, consisting of the amino acid sequence of Seq. Id. No.5.

6. An isolated antigen protein of black-lip pearl oyster egg extract, consisting of the amino acid sequence of Seq. Id. No.6.

7. An isolated antigen protein of black-lip pearl oyster egg extract, consisting of the amino acid sequence of Seq. Id. No.7.

8. An isolated antigen protein of black-lip pearl oyster egg extract, consisting of the amino acid sequence of Seq. Id. No.8.

9. An isolated antibody specific to the antigen protein defined in any one of claims 1 to 8.

10. A method of quantitative assessment of reproductive effort of black-lip pearl oysters, comprising the steps of:
   (i) contacting a sample of egg protein of black-lip pearl oysters with the antibody of claim 9;
   (ii) measuring a reactivity of the egg protein of black-lip pearl oysters in said sample and said antibody via an antigen-antibody reaction; and
   (iii) determining an amount of the egg protein of black-lip pearl oysters in the sample by plotting the reactivity determined in step (ii) on a standard curve of reactivities of actual amounts of the egg protein of black-lip pearl oysters, thereby assessing the reproductive effort of black-lip pearl oysters.

11. The method as claimed in claim 10, wherein the antigen-antibody reaction is ELISA (enzyme-linked immunosorbent assay).

* * * * *